(12) United States Patent
Locke et al.

(10) Patent No.: US 11,229,732 B2
(45) Date of Patent: *Jan. 25, 2022

(54) SYSTEM AND METHOD FOR LOCATING FLUID LEAKS AT A DRAPE OF A REDUCED PRESSURE DELIVERY SYSTEM

(71) Applicant: KCI Licensing, Inc., San Antonio, TX (US)

(72) Inventors: Christopher Brian Locke, Bournemouth (GB); Mark Stephen James Beard, Ferndown (GB); David Robson Blandford, Alderholt (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 440 days.

This patent is subject to a terminal disclaimer.

(21) Appl. No.: 16/257,999

(22) Filed: Jan. 25, 2019

(65) Prior Publication Data

US 2019/0151516 A1     May 23, 2019

Related U.S. Application Data

(60) Continuation of application No. 15/275,008, filed on Sep. 23, 2016, now Pat. No. 10,232,095, which is a (Continued)

(51) Int. Cl.
*A61M 1/00* (2006.01)
*A61M 5/14* (2006.01)
(Continued)

(52) U.S. Cl.
CPC ............ *A61M 1/74* (2021.05); *A61H 9/0057* (2013.01); *A61M 1/0001* (2013.01);
(Continued)

(58) Field of Classification Search
CPC .. A61M 1/0001; A61M 1/0023; A61M 1/604; A61M 1/73; A61M 1/74; A61M 1/90; A61M 5/1415
See application file for complete search history.

(56) References Cited

U.S. PATENT DOCUMENTS 1,355,846 A    10/1920  Rannells
1,885,926 A    11/1932  Lewis
(Continued)

FOREIGN PATENT DOCUMENTS

AU    550575 B2    3/1986
AU    745271 B2    3/2002
(Continued)

OTHER PUBLICATIONS

Extended European Search Report for corresponding Application No. EP17159742.0, dated Aug. 1, 2017.
(Continued)

*Primary Examiner* — Adam Marcetich

(57) ABSTRACT

A system and method for performing tissue therapy may include applying a reduced pressure to a tissue site, sensing a fluid parameter being applied to the tissue site, generating a fluid sensor signal in response to sensing the fluid parameter, and altering the fluid sensor signal in response to sensing that the fluid parameter changes. A fluid leak location mode may be entered. In response to the fluid leak location mode being entered, a graphical user interface that provides for fluid leak location functionality may be displayed. In one embodiment, the fluid leak location mode may be automatically entered in response to the sensor signal crossing a threshold value. Additionally, an alarm signal may be generated in response to determining that the fluid sensor signal crosses the threshold value.

29 Claims, 7 Drawing Sheets

Related U.S. Application Data continuation of application No. 13/948,757, filed on Jul. 23, 2013, now Pat. No. 9,474,679, which is a continuation of application No. 13/274,951, filed on Oct. 17, 2011, now Pat. No. 8,500,718, which is a division of application No. 11/901,657, filed on Sep. 18, 2007, now Pat. No. 8,061,360.

(60) Provisional application No. 60/845,993, filed on Sep. 19, 2006.

(51) Int. Cl.

| | | |
|---|---|---|
| *F16M 11/04* | (2006.01) | |
| *F16M 13/02* | (2006.01) | |
| *G01F 23/14* | (2006.01) | |
| *A61N 1/04* | (2006.01) | |
| *A61N 5/06* | (2006.01) | |
| *A61H 9/00* | (2006.01) | |

(52) U.S. Cl.
CPC .......... *A61M 1/0023* (2013.01); *A61M 1/604* (2021.05); *A61M 1/73* (2021.05); *A61M 1/90* (2021.05); *A61M 5/1415* (2013.01); *A61N 1/0468* (2013.01); *A61N 5/0616* (2013.01); *F16M 11/046* (2013.01); *F16M 11/048* (2013.01); *F16M 13/02* (2013.01); *G01F 23/14* (2013.01); *A61M 2201/5056* (2013.01); *A61M 2205/15* (2013.01); *A61M 2205/18* (2013.01); *A61M 2205/33* (2013.01); *A61M 2205/3327* (2013.01); *A61M 2205/3331* (2013.01); *A61M 2205/3334* (2013.01); *A61M 2205/3337* (2013.01); *A61M 2205/3344* (2013.01); *A61M 2205/3379* (2013.01); *A61M 2205/43* (2013.01); *A61M 2205/50* (2013.01); *A61M 2205/502* (2013.01); *A61M 2205/581* (2013.01); *A61M 2205/583* (2013.01); *A61N 2005/0661* (2013.01); *F16M 2200/027* (2013.01)

(56) References Cited

U.S. PATENT DOCUMENTS

| | | |
|---|---|---|
| 2,547,758 A | 4/1951 | Keeling |
| 2,632,443 A | 3/1953 | Lesher |
| 2,682,873 A | 7/1954 | Evans et al. |
| 2,696,113 A | 12/1954 | Prescott |
| 2,910,763 A | 11/1959 | Lauterbach |
| 2,969,057 A | 1/1961 | Simmons |
| 3,012,772 A | 12/1961 | Gunzner |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,902,495 A | 9/1975 | Weiss et al. |
| 4,018,908 A | 4/1977 | Gross |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,338,945 A | 7/1982 | Kosugi et al. |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,509,959 A | 4/1985 | McCombs |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,547,092 A | 10/1985 | Vetter et al. |
| 4,548,202 A | 10/1985 | Duncan |
| 4,551,139 A | 11/1985 | Plaas et al. |
| 4,553,431 A | 11/1985 | Nicolai |
| 4,569,348 A | 2/1986 | Hasslinger |
| 4,569,674 A | 2/1986 | Phillips et al. |
| 4,583,546 A | 4/1986 | Garde |
| 4,605,399 A | 8/1986 | Weston et al. |
| 4,608,041 A | 8/1986 | Nielsen |
| 4,608,857 A | 9/1986 | Mertens et al. |
| 4,640,688 A | 2/1987 | Hauser |
| 4,651,743 A | 3/1987 | Stoller |
| 4,655,754 A | 4/1987 | Richmond et al. |
| 4,664,662 A | 5/1987 | Webster |
| 4,673,272 A | 6/1987 | Suzuki et al. |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,785,659 A | 11/1988 | Rose et al. |
| 4,787,888 A | 11/1988 | Fox |
| 4,826,494 A | 5/1989 | Richmond et al. |
| 4,835,522 A * | 5/1989 | Andrejasich ............ G01M 3/32 340/521 |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,073,172 A | 12/1991 | Fell |
| 5,086,170 A | 2/1992 | Luheshi et al. |
| 5,092,858 A | 3/1992 | Benson et al. |
| 5,100,396 A | 3/1992 | Zamierowski |
| 5,108,213 A | 4/1992 | Shields |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,195,995 A | 3/1993 | Walker |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,310,524 A | 5/1994 | Campbell et al. |
| 5,342,376 A | 8/1994 | Ruff |
| 5,343,878 A | 9/1994 | Scarberry et al. |
| 5,344,415 A | 9/1994 | DeBusk et al. |
| 5,358,494 A | 10/1994 | Svedman |
| 5,407,310 A | 4/1995 | Kassouni |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |

(56) References Cited

U.S. PATENT DOCUMENTS

| | | |
|---|---|---|
| 5,607,388 A | 3/1997 | Ewall |
| 5,636,643 A | 6/1997 | Argenta et al. |
| 5,645,081 A | 7/1997 | Argenta et al. |
| 5,658,322 A | 8/1997 | Fleming |
| 5,690,815 A | 11/1997 | Krasnoff et al. |
| 5,718,562 A | 2/1998 | Lawless et al. |
| 5,749,842 A | 5/1998 | Cheong et al. |
| 5,752,688 A | 5/1998 | Campbell et al. |
| 5,852,675 A | 12/1998 | Matsuo et al. |
| 5,862,803 A | 1/1999 | Besson et al. |
| 5,911,687 A | 6/1999 | Sato et al. |
| 5,986,163 A | 11/1999 | Augustine |
| 6,032,678 A | 3/2000 | Rottem |
| 6,036,296 A | 3/2000 | Axtell et al. |
| 6,047,259 A | 4/2000 | Campbell et al. |
| 6,057,689 A | 5/2000 | Saadat |
| 6,071,267 A | 6/2000 | Zamierowski |
| 6,091,981 A | 7/2000 | Cundari et al. |
| 6,134,003 A | 10/2000 | Tearney et al. |
| 6,135,116 A | 10/2000 | Vogel et al. |
| 6,142,982 A | 11/2000 | Hunt et al. |
| 6,208,749 B1 | 3/2001 | Gutkowicz-Krusin et al. |
| 6,241,747 B1 | 6/2001 | Ruff |
| 6,287,316 B1 | 9/2001 | Agarwal et al. |
| 6,292,866 B1 | 9/2001 | Zaiki et al. |
| 6,345,623 B1 | 2/2002 | Heaton et al. |
| 6,378,826 B1 | 4/2002 | Knaub et al. |
| 6,447,537 B1 | 9/2002 | Hartman |
| 6,453,247 B1 | 9/2002 | Hunaidi |
| 6,458,109 B1 | 10/2002 | Henley et al. |
| 6,471,197 B1 | 10/2002 | Denk et al. |
| 6,488,643 B1 | 12/2002 | Tumey et al. |
| 6,493,568 B1 | 12/2002 | Bell et al. |
| 6,529,006 B1 | 3/2003 | Hayes |
| 6,553,998 B2 | 4/2003 | Heaton et al. |
| 6,568,282 B1* | 5/2003 | Ganzi ............... B01D 65/102 73/38 |
| 6,648,862 B2 | 11/2003 | Watson |
| 6,663,586 B2 | 12/2003 | Verkaart et al. |
| 6,733,537 B1 | 5/2004 | Fields et al. |
| 6,814,079 B2 | 11/2004 | Heaton et al. |
| 6,915,950 B1 | 7/2005 | Legerstee |
| 7,004,915 B2 | 2/2006 | Boynton et al. |
| 7,100,244 B2 | 9/2006 | Qin et al. |
| 7,198,046 B1 | 4/2007 | Argenta et al. |
| 7,770,855 B2 | 8/2010 | Locke et al. |
| 7,846,141 B2 | 12/2010 | Weston |
| 7,857,271 B2 | 12/2010 | Lees |
| 7,876,546 B2 | 1/2011 | Locke et al. |
| 8,000,777 B2 | 8/2011 | Jaeb et al. |
| 8,057,449 B2 | 11/2011 | Sanders et al. |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,366,690 B2 | 2/2013 | Locke et al. |
| 8,398,614 B2 | 3/2013 | Blott et al. |
| 8,449,509 B2 | 5/2013 | Weston |
| 8,500,718 B2 | 8/2013 | Locke et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,690,845 B2 | 4/2014 | Long et al. |
| 8,696,662 B2 | 4/2014 | Eder et al. |
| 8,786,999 B2 | 7/2014 | Locke et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,019,681 B2 | 4/2015 | Locke et al. |
| 9,198,801 B2 | 12/2015 | Weston |
| 9,211,365 B2 | 12/2015 | Weston |
| 9,289,542 B2 | 3/2016 | Blott et al. |
| 9,320,673 B2 | 4/2016 | Locke et al. |
| 2002/0019751 A1 | 2/2002 | Rothschild et al. |
| 2002/0077661 A1 | 6/2002 | Saadat |
| 2002/0095198 A1 | 7/2002 | Whitebook et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0198503 A1 | 12/2002 | Risk et al. |
| 2002/0198504 A1 | 12/2002 | Risk et al. |
| 2003/0022645 A1 | 1/2003 | Runzo |
| 2003/0085908 A1 | 5/2003 | Luby |
| 2003/0088371 A1* | 5/2003 | Parker ............... G01M 3/36 702/36 |
| 2003/0182806 A1 | 10/2003 | Luebke et al. |
| 2003/0226943 A1 | 12/2003 | Laisement et al. |
| 2004/0008523 A1 | 1/2004 | Butler |
| 2004/0070535 A1 | 4/2004 | Olsson et al. |
| 2004/0073151 A1 | 4/2004 | Weston |
| 2004/0078236 A1 | 4/2004 | Stoodley et al. |
| 2004/0122705 A1 | 6/2004 | Sabol et al. |
| 2004/0138632 A1 | 7/2004 | Bemis et al. |
| 2004/0143677 A1 | 7/2004 | Novak |
| 2004/0154379 A1* | 8/2004 | Enquist ............... G01M 3/20 73/40.7 |
| 2004/0231414 A1 | 11/2004 | Delnevo |
| 2005/0051168 A1 | 3/2005 | DeVries et al. |
| 2005/0090787 A1 | 4/2005 | Risk et al. |
| 2005/0102009 A1 | 5/2005 | Costantino |
| 2005/0115314 A1 | 6/2005 | Meagher |
| 2005/0120792 A1 | 6/2005 | Merrild |
| 2005/0126265 A1* | 6/2005 | Herzog ............... G01M 3/3236 73/49.2 |
| 2005/0148913 A1 | 7/2005 | Weston |
| 2005/0203469 A1 | 9/2005 | Bobroff et al. |
| 2005/0261642 A1 | 11/2005 | Weston |
| 2006/0027979 A1 | 2/2006 | Yang et al. |
| 2006/0072804 A1 | 4/2006 | Watson et al. |
| 2006/0074722 A1 | 4/2006 | Chu |
| 2006/0131350 A1 | 6/2006 | Schechter et al. |
| 2006/0189887 A1 | 8/2006 | Hassler et al. |
| 2006/0195625 A1 | 8/2006 | Hesse |
| 2006/0252991 A1* | 11/2006 | Kubach ............... G01M 3/26 600/118 |
| 2007/0000310 A1 | 1/2007 | Yamartino et al. |
| 2007/0032763 A1 | 2/2007 | Vogel |
| 2007/0053554 A1 | 3/2007 | Fayad et al. |
| 2007/0125170 A1 | 6/2007 | Tenney |
| 2007/0265586 A1 | 11/2007 | Joshi et al. |
| 2008/0008370 A1 | 1/2008 | Chio |
| 2008/0260218 A1 | 10/2008 | Smith et al. |
| 2008/0275409 A1 | 11/2008 | Kane et al. |
| 2008/0276692 A1* | 11/2008 | Wetzig ............... G01M 3/205 73/40.7 |
| 2008/0281281 A1 | 11/2008 | Meyer et al. |
| 2009/0120165 A1 | 5/2009 | Lang et al. |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| DE | 29920378 U1 | 3/2000 |
| EP | 0100148 A1 | 2/1984 |
| EP | 0117632 A2 | 9/1984 |
| EP | 0161865 A2 | 11/1985 |
| EP | 0224367 A2 | 6/1987 |
| EP | 0358302 A2 | 3/1990 |
| EP | 0836831 A2 | 4/1998 |
| EP | 1018967 A1 | 7/2000 |
| EP | 1591713 A1 | 11/2005 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |

(56) References Cited

FOREIGN PATENT DOCUMENTS

| GB | 2 329 127 A | 3/1999 |
|---|---|---|
| GB | 2 333 965 A | 8/1999 |
| GB | 2356148 A | 5/2001 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 94/21312 A2 | 9/1994 |
| WO | 96/05873 A1 | 2/1996 |
| WO | 97/18007 A1 | 5/1997 |
| WO | 97047235 A1 | 12/1997 |
| WO | 1998025122 A1 | 6/1998 |
| WO | 99/13793 A1 | 3/1999 |
| WO | 9949775 A2 | 10/1999 |
| WO | 2000021586 A1 | 4/2000 |
| WO | 02080764 A1 | 10/2002 |
| WO | 2005060466 A2 | 7/2005 |
| WO | 2005061025 A1 | 7/2005 |
| WO | 2006052745 A2 | 5/2006 |

OTHER PUBLICATIONS

Indian First Examination Report corresponding to Application No. 2076/CHENP/2009, dated Jul. 14, 2017.
Extended European Search Report corresponding to Application No. 17157187.0 dated Jul. 21, 2017.
European Examination Report for corresponding Application No. 078385614, dated May 25, 2016.
Indian Exam Report for corresponding application 2074CHENP2009, dated Sep. 25, 2017.
Extended European Search Report for corresponding Application No. 171794498, dated Nov. 8, 2017.
Indian Hearing Notice for corresponding Application No. 2076/CHENP/2009, dated Jul. 30, 2018.
Brazilian Technical Opinion for corresponding Application No. PI0714993-0, mailed Jun. 14, 2018.
Extended European Search Report for corresponding EP07838545.7, dated Aug. 2, 2013.
Brazilian Preliminary Examination Report for corresponding Application No. PI0714531-4, dated Feb. 26, 2019.
Brazilian Preliminary Examination Report for Corresponding Application No. PI 0715020-2, dated Jun. 30, 2020.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.

(56) References Cited

OTHER PUBLICATIONS

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96,167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

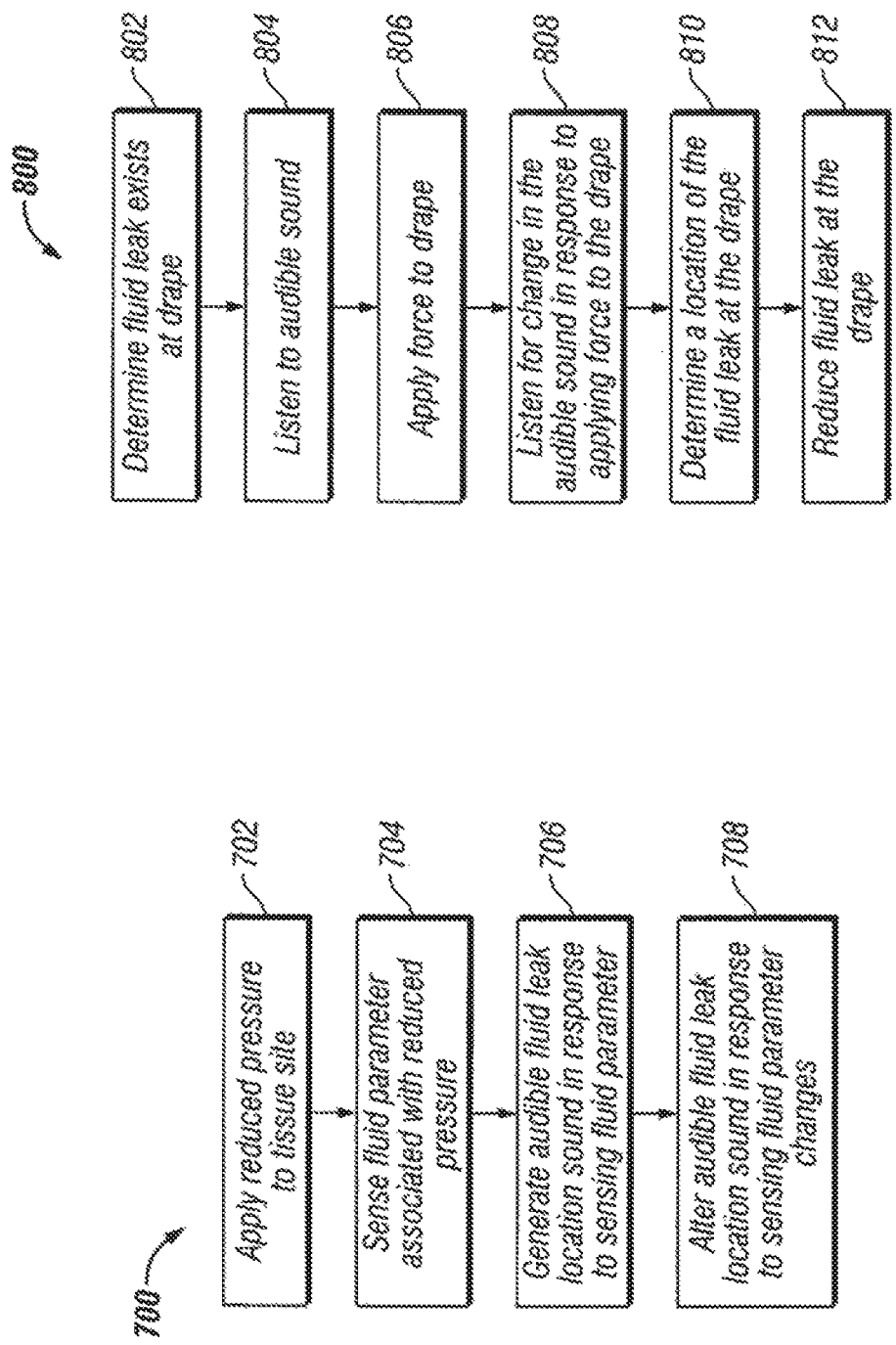

SYSTEM AND METHOD FOR LOCATING FLUID LEAKS AT A DRAPE OF A REDUCED PRESSURE DELIVERY SYSTEM

CROSS-REFERENCE TO RELATED APPLICATIONS

This Application is a continuation of U.S. patent application Ser. No. 15/275,008, entitled "SYSTEM AND METHOD FOR LOCATING FLUID LEAKS AT A DRAPE OF A REDUCED PRESSURE DELIVERY SYSTEM," filed Sep. 23, 2016; which is a continuation of U.S. patent application Ser. No. 13/948,757, entitled "SYSTEM AND METHOD FOR LOCATING FLUID LEAKS AT A DRAPE OF A REDUCED PRESSURE DELIVERY SYSTEM," filed Jul. 23, 2013, now U.S. Pat. No. 9,474,679; which is a continuation of U.S. patent application Ser. No. 13/274,951, entitled "SYSTEM AND METHOD FOR LOCATING FLUID LEAKS AT A DRAPE OF A REDUCED PRESSURE DELIVERY SYSTEM," filed Oct. 17, 2011, now U.S. Pat. No. 8,500,718; which is a divisional of U.S. patent application Ser. No. 11/901,657, entitled "SYSTEM AND METHOD FOR LOCATING FLUID LEAKS AT A DRAPE OF A REDUCED PRESSURE DELIVERY SYSTEM," filed on Sep. 18, 2007, now U.S. Pat. No. 8,061,360, which claims priority to Provisional Patent Application Ser. No. 60/845,993, entitled "REDUCED PRESSURE DELIVERY SYSTEM FOR ADMINISTERING A REDUCED PRESSURE TISSUE TREATMENT TO A TISSUE SITE," filed Sep. 19, 2006; all of which are herein incorporated by reference in their entirety.

BACKGROUND OF THE INVENTION

1. Field of the Invention

This invention relates generally to a system and method of promoting tissue growth, and more specifically, a method for detecting and correcting fluid leaks at a drape positioned at a tissue site being treated by a reduced pressure delivery system.

2. Description of Related Art

Tissue growth and wound healing of patients has been shown to be accelerated through the use of applying reduced pressure to a tissue site. Reduced pressure delivery systems operate to form such a reduced pressure at a tissue site of a patient. This form of wound healing can be readily integrated into a clinician's wound healing procedures. Reduced pressure tissue therapy optimizes patient care and decreases costs associated with treatment of patients having traumatic and chronic wounds. Reduced pressure therapy can be administered in hospitals, community settings, such as assisted living complexes and convalescences homes, or homes of patients.

Reduced pressure delivery to a wound or tissue site promotes wound healing and/or tissue growth, in part, by removing infectious materials and other fluids from the wound or tissue site. Reduced pressure treatment further promotes tissue growth by imposing forces on the tissue, thereby causing micro-deformation of the tissue, which is believed to contribute to the development of granulation tissue at the tissue site. The forces imposed on the tissue site by the delivery of reduced pressure further encourages improved blood flow at the tissue site, which further assists in the growth of new tissue.

Reduced pressure delivery systems generally use a vacuum pump to apply a reduced pressure via a reduced pressure conduit to a tissue site. A manifold is often used at the tissue site to help evenly distribute the reduced pressure. A drape is typically used to cover the manifold and form a seal with surrounding tissue of the tissue site to which the reduced pressure is being applied. So that the reduced pressure remains constant and accurate, thereby providing optimum tissue growth and/or therapy, the drape is to be interfaced and maintained with the surrounding tissue of the tissue site to prevent fluid leaks, such as air leaks. In the event that a fluid leak results during installation of the drape or during treatment, clinicians often find it difficult to isolate the precise location of the fluid leak. If the fluid leak is not corrected, then the performance of the reduced pressure delivery system is reduced and full treatment potential is not realized.

SUMMARY OF THE INVENTION

To overcome the problem of locating fluid leaks at an interface between a drape and tissue of a patient, the principles of the present invention provide for detecting location of and correcting fluid leaks at the drape of reduced pressure delivery systems. By being able to locate fluid leaks at the drape and tissue interface, optimum therapeutic results may be produced.

One embodiment of a system for performing tissue therapy may include a processing unit. The system may include a reduced pressure source, a conduit fluidly connected between said reduced pressure source and a tissue site of a patient, where the conduit may be configured to apply a reduced pressure produced by the reduced pressure source to the tissue site. A drape may be configured for positioning over the tissue site to maintain the reduced pressure at the tissue site. A fluid sensor may be in fluid communication with the conduit and electrical communication with the processing unit. The fluid sensor may be configured to sense a fluid parameter within the conduit, and to generate a fluid sensor signal in response to sensing the fluid parameter. The fluid sensor may alter the fluid sensor signal in response to sensing that the fluid parameter within the conduit changes. An electronic display may be in communication with the processing unit. The processing unit may be configured to enter a fluid leak location mode that causes a graphical user interface that provides for fluid leak location functionality to be displayed on the electronic display. In one embodiment, the fluid leak location mode may be automatically entered in response to the fluid sensor signal crossing a threshold value. Additionally, an alarm signal may be generated in response to determining that the fluid sensor signal crosses the threshold value.

One embodiment of a method for performing tissue therapy may include applying a reduced pressure to a tissue site, sensing a fluid parameter being applied to the tissue site, generating a fluid sensor signal in response to sensing the fluid parameter, and altering the fluid sensor signal in response to sensing that the fluid parameter changes. A fluid leak location mode may be entered. In response to the fluid leak location mode being entered, a graphical user interface that provides for fluid leak location functionality may be displayed. In one embodiment, the fluid leak location mode may be automatically entered in response to the sensor signal crossing a threshold value. Additionally, an alarm signal may be generated in response to determining that the fluid sensor signal crosses the threshold value.

BRIEF DESCRIPTION OF THE DRAWINGS

A more complete understanding of the method and apparatus of the present invention may be obtained by reference to the following Detailed Description when taken in conjunction with the accompanying Drawings wherein:

FIG. 7 is a flow chart of an exemplary process for generating an audible fluid leak location sound to notify a user that a fluid leak exist at the drape;

FIG. 8 is a flow chart of an exemplary process for a user to locate a fluid leak at the drape.

DETAILED DESCRIPTION OF THE PRESENT INVENTION

Figure 1:
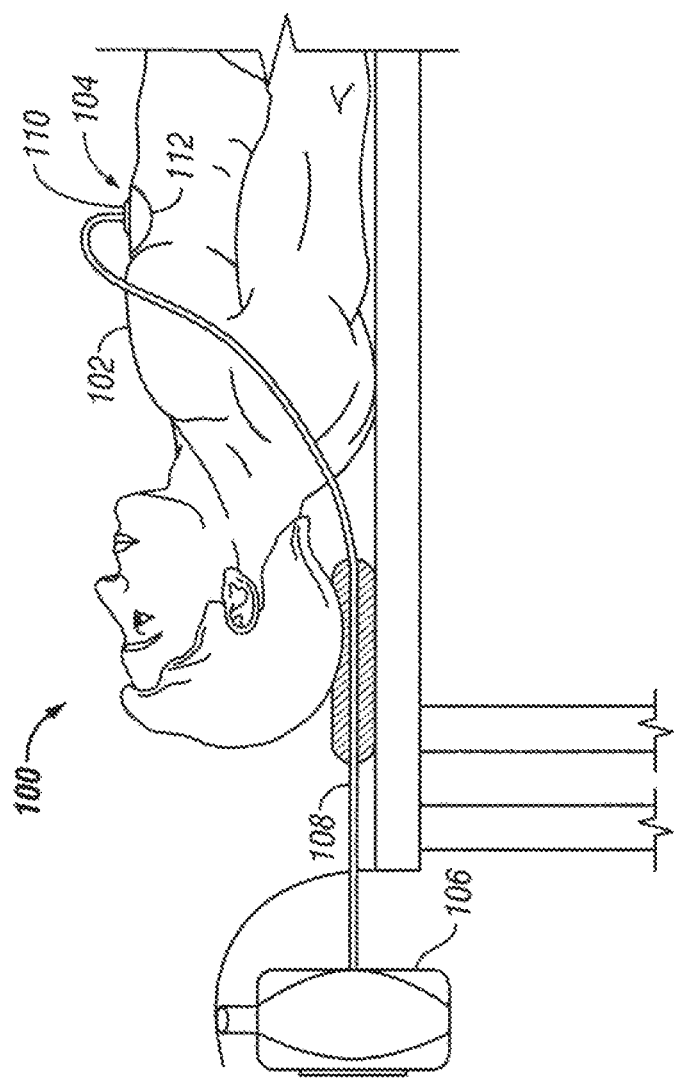
FIG. 1 is an illustration of an exemplary configuration of a patient being treated using a reduced pressure delivery system.

With regard to FIG. 1, a setup 100 for treating a patient 102 is shown. The patient is receiving reduced pressure treatment at a tissue site 104 by a reduced pressure delivery system 106. The reduced pressure delivery system 106 may include a reduced pressure conduit 108 that extends from the reduced pressure delivery system 106 to the tissue site 104. At the tissue site 104, a reduced pressure dressing or distribution manifold 110 may be fluidly connected to the reduced pressure conduit 108. In addition, a drape 112 may be placed over the tissue site 104 and distribution manifold 110. The drape 112 may be a flexible material that is impermeable to gases to prevent air or other fluids from entering or exiting the tissue site 104 during reduced pressure treatment.

As used herein, the term "flexible" refers to an object or material that is able to be bent or flexed. Elastomer materials are typically flexible, but reference to flexible materials herein does not necessarily limit material selection to only elastomers. The use of the term "flexible" in connection with a material or reduced pressure delivery apparatus in accordance with the principles of the present invention generally refers to the material's ability to conform to or closely match the shape of a tissue site. For example, the flexible nature of a reduced pressure delivery apparatus used to treat a bone defect may allow the apparatus to be wrapped or folded around the portion of the bone having the defect.

The term "fluid" as used herein generally refers to a gas or liquid, but may also include any other flowable material, including but not limited to gels, colloids, and foams. One example of a gas is air.

The term "impermeable" as used herein generally refers to the ability of a membrane, cover, sheet, or other substance to block or slow the transmission of either liquids or gas. Impermeable may be used to refer to covers, sheets, or other membranes that are resistant to the transmission of liquids, while allowing gases to transmit through the membrane. While an impermeable membrane may be liquid type, the membrane may simply reduce the transmission rate of all or only certain liquids. The use of the term "impermeable" is not meant to imply that an impermeable membrane is above or below any particular industry standard measurement for impermeability, such as a particular value of water vapor transfer rate (WVTR).

The term "manifold" as used herein generally refers to a substance or structure that is provided to assist in applying reduced pressure to, delivering fluids to, or removing fluids from a tissue site. A manifold typically includes a plurality of flow channels or pathways that interconnect to improve distribution of fluids provided to and removed from the area of tissue around the manifold. Examples of manifolds may include, without limitation, devices that have structural elements arranged to form slow channels, cellular foams, such as open-desk cell foam, porous tissue collections, and liquids, gels and foams that include or cure to include flow channels.

The term "reduced pressure" as used herein generally refers to a pressure less than the ambient pressure at a tissue site that is being subjected to treatment. In most cases, this reduced pressure will be less than the atmosphere pressure at which the patient is located. Alternatively, the reduced pressure may be less than a hydrostatic pressure of tissue at the tissue site. Although the terms "vacuum" and "negative pressure" may be used to describe the pressure applied to the tissue site, the actual pressure applied to the tissue site may be significantly less than the pressure normally associated with a complete vacuum. Reduced pressure may initially generate fluid flow in the tube or conduit in the area of the tissue site. As the hydrostatic pressure around the tissue site approaches the desired reduced pressure, the flow may subside, and the reduced pressure is then maintained. Unless otherwise indicated, values of pressures stated herein are gage pressures.

The term "scaffold" as used herein refers to a substance or structure used to enhance or promote the growth of cells and/or the formation of tissue. A scaffold is typically a three dimensional porous structure that provides a template for cell growth. The scaffold may be infused with, coated with, or comprised of cells, growth factors, or other nutrients to promote cell growth. A scaffold may be used as a manifold in accordance with the embodiments described herein to administer reduced pressure tissue treatment to a tissue site.

The term "tissue site" as used herein refers to a wound or defect located on or within any tissue, including but not limited to, bone tissue, adipose tissue, muscle tissue, neuro tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue.

For example, reduced pressure tissue treatment may be used in certain tissue areas to grow additional tissue that may be harvested and transplanted to another tissue location.

The term "clinician" is used herein as meaning any medical professional, user, family member of a patient, or patient who interacts or interfaces with a reduced pressure delivery system.

Figure 2:
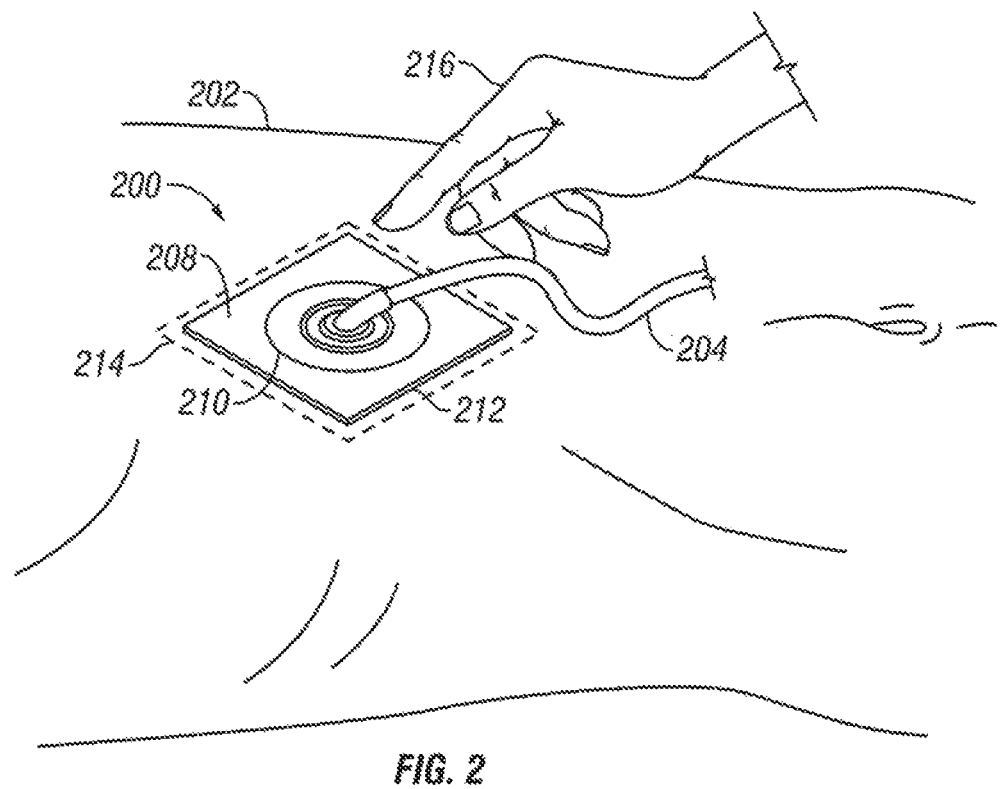
FIG. 2 is an illustration of an exemplary drape covering a tissue site to which reduced pressure is being applied by a reduced pressure delivery system.

With regard to FIG. 2, a tissue site 200 on a person's body 202 is receiving reduced pressure therapy from a reduced pressure delivery system (not shown). The reduced pressure delivery system is connected to a reduced pressure conduit 204 and in fluid communication with a distribution manifold (not shown), either directly or via an adapter 206. A drape 208 may be configured to cover the distribution manifold, which is shown to be pressing into the drape 208 to form an outline 210. The drape 208 covers the tissue site 200, thereby helping to maintain a seal at the tissue site so that fluids, such as air, cannot enter or exit the tissue site. By preventing fluids from entering or exiting the tissue site 200, the tissue site 200 may receive maximum benefit of the reduced pressure therapy, including minimizing chance for additional infection and improving growth of tissue.

In establishing a dressing, which may include the distribution manifold and drape 208, at the tissue site 200, a clinician may apply the dressing and apply a force to the drape 208 during operation of the reduced pressure delivery system. By applying a force along outer edges of the drape 208, the clinician may create or otherwise alter a seal at an intersection 212 of the drape 208 and tissue 214 surrounding the tissue site 200. In the event that the seal is not completely formed or a fluid leak develops at the drape 208, the clinician may press his or her finger 216 along the outer edges 212 of the drape 208 to improve or re-establish the seal. Because locating a fluid leak at the drape 208 is often difficult in practice, the principles of the present invention provide a system and method for determining location of the fluid leak, as further described herein with respect to FIGS. 4-8.

Figure 3:
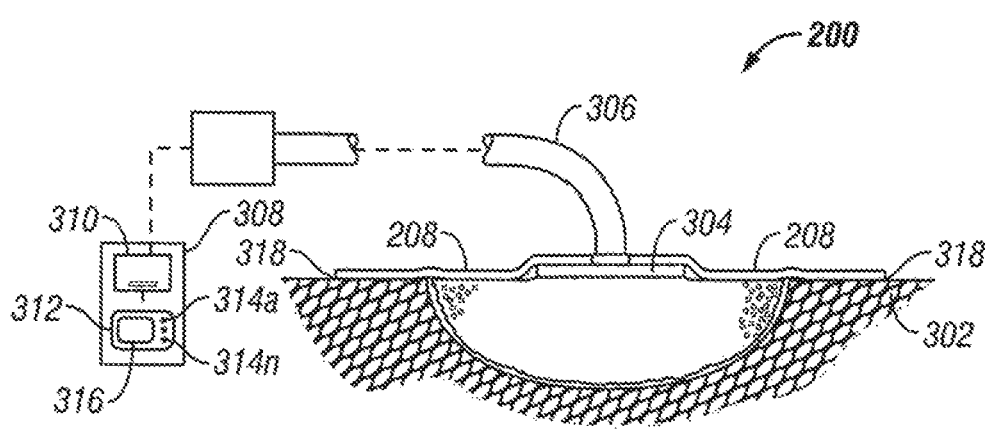
FIG. 3 is an illustration of an exemplary drape covering a tissue site to which reduced pressure is being applied by a reduced pressure delivery system.

With regard to FIG. 3, a cutout view of the tissue site 200 is provided to show the drape 208 extending over healthy tissue 302 surrounding the tissue site 200. The drape 208 extends over manifold 304, which is in fluid communication with reduced pressure conduit 306. The reduced pressure conduit 306 is further in fluid communication with reduced pressure delivery system 308. The reduced pressure therapy system 308 may include a vacuum pump 310 and electronic display 312. The electronic display 312 may include control elements 314a-314n (collectively 314) that may be used by a user operating the reduced pressure delivery system 308. In addition or alternatively, the electronic display 312 may include a touch-screen electronic display 316 that enables the user to interface with and operate the reduced pressure delivery system 308.

The drape 208 that extends over the healthy tissue 302 forms a seal at an intersection 318 where the healthy tissue 302 and drape 208 contact one another. If a fluid leak develops at the intersection 318 (i.e., at the tissue site 200), then a fluid leak sensor (not shown) may generate and communicate a fluid leak signal. The fluid leak signal may be indicative of a fluid parameter indicative of or responsive to the fluid leak crossing a predetermined threshold level. A processing unit (not shown) may respond by generating a fluid leak alarm in an audible and/or visual manner. For example, a buzzer, bell, recorded message, or other audible sound may be generated to alert a clinician that a fluid leak has occurred at the drape 208. To locate the fluid leak at the drape 208, a fluid leak location mode may be automatically or manually entered at the reduced pressure delivery system 308. The fluid leak location mode may be used to enable the clinician to apply a force, such as pressing a finger along the drape 208, such as pressing at the intersection 318. As the clinician applies the force, in response to the clinician applying a force to the location of the fluid leak, the reduced pressure delivery system 308 may generate an audible sound that changes. The audible sound may be decreased in pitch or volume, for example, to enable the clinician to identify a location at the drape 208 at which a fluid leak exists.

Figure 4:
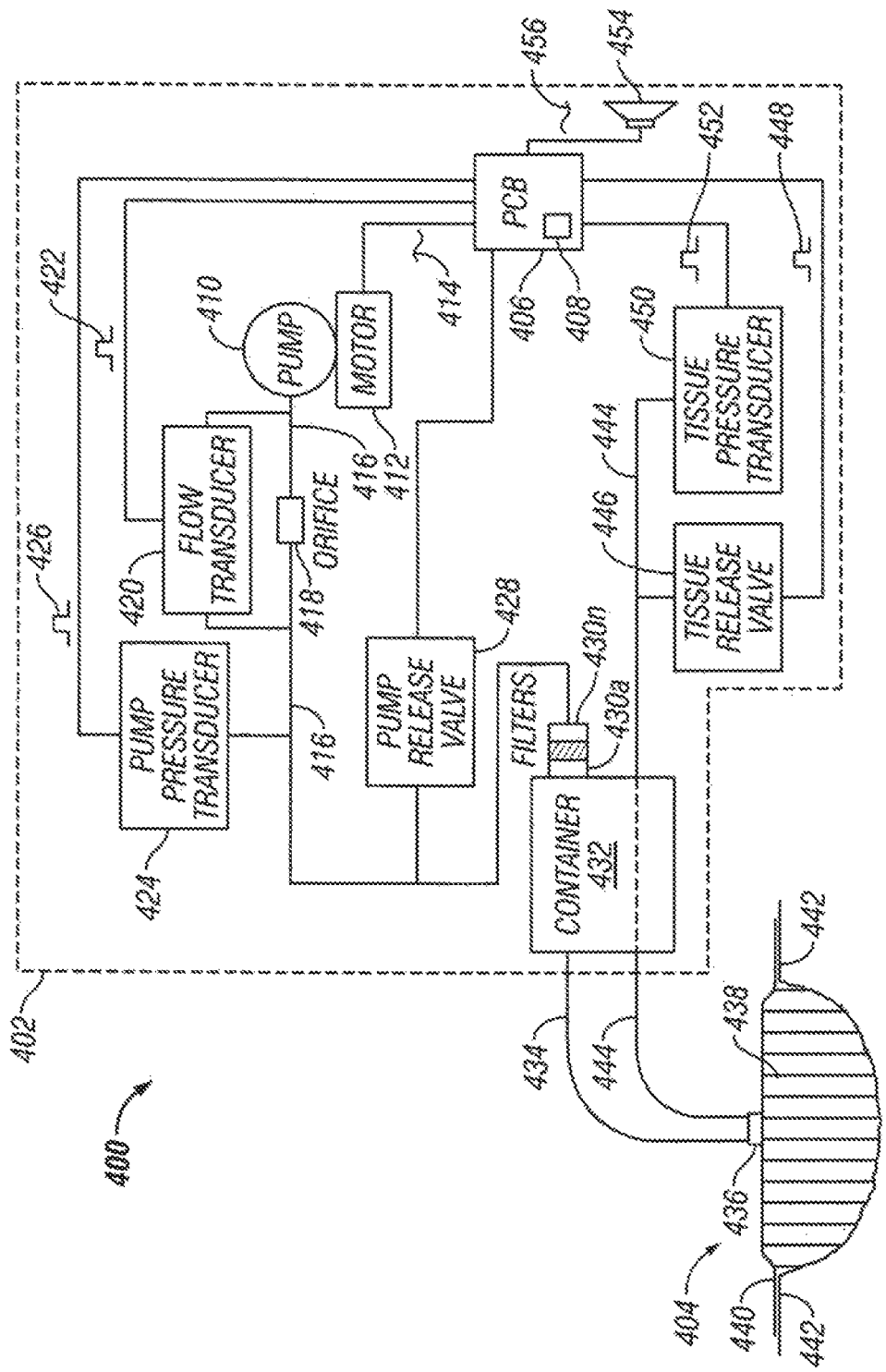
FIG. 4 is a block diagram of an exemplary reduced pressure delivery system configured to apply reduced pressure to a tissue site and notify a clinician that a fluid leak is occurring at the drape.

With regard to FIG. 4, a configuration 400 of a reduced pressure delivery system 402 is shown to be operating to apply a reduced pressure to tissue site 404. The reduced pressure delivery system 402 may include a printed circuit board 406 that includes a processing unit 408. The processing unit 408 may include one or more processors, logic, analog components, or any other electronics that enable signals including information, such as fluid pressure at a tissue site, to be received. The processing unit 408 may process the information provided by the signals. For example, a fluid leak signal may be received by the processing unit 408 and a fluid leak alarm and/or fluid leak location process may be driven by the processing unit 408.

The reduced pressure delivery system 402 may further include a pump 410, such as a vacuum pump, that may be driven by a motor 412. The motor 412 may be in electrical communication with the PCB 406 and respond to control signals 414 generated by the PCB 406. The pump 410 may be fluidly connected to a reduced pressure conduit 416. The reduced pressure conduit 416 may include an orifice 418 that operates as a relief valve. In parallel with the orifice is a flow transducer 420 that may be configured to determine flow rate of fluid passing through the reduced pressure conduit 416. The flow transducer 420 is fluidly connected to the reduced pressure conduit 416 and configured to generate a flow rate signal 422 including information indicative of flow rate of a fluid within the reduced pressure conduit 416. The flow rate signal 422 may be digital or analog.

A pump pressure transducer 424 may be connected to reduced pressure conduit 416 to convert pressure in the reduced pressure conduit 416 and communicate a pump pressure signal 426 including information indicative of fluid pressure in the reduced pressure conduit 416 to the PCB 406. The pump pressure signal 426 may be digital or analog. A pump release valve 428 may also be connected to the reduced pressure conduit 416 and be configured to release pressure from the reduced pressure conduit 416 in case of an emergency situation or otherwise.

The reduced pressure delivery system 402 may further include one or more filters 430a-430n (collectively 430) that are in fluid communication with the reduced pressure conduit 416. The filters 430 may be in fluid communication with container 432, which is used to collect fluids from tissue site 404. The filters 430 may be configured to prevent fluids collected in the container 432 from entering the reduced pressure conduit 416. The container 432 may further be in fluid communication with reduced pressure conduit 434. Although shown as separate conduits, the reduced pressure conduits 416 and 434 may be the same or different material and have the same or different dimensions. The reduced pressure conduit 434 may connect to or be in fluid communication with an adapter 436, which may be connected to a distribution manifold 438 to evenly distribute reduced pressure across the tissue site 404. Drape 440, which extends over the tissue site and onto tissue 442 surrounding the tissue site 404 being treated by the reduced pressure is used to form a seal to form and maintain reduced pressure at the tissue site 404.

A feedback reduced pressure conduit 444 may pass through container 432. A tissue release valve 446 may be connected to the feedback reduced pressure conduit 444 to enable pressure to be released at the tissue site 404 in response to a command signal 448 generated by the processing unit 408. The command signal 448 may be generated by the processing unit 408 in response to the processing unit 408 receiving a sensor signal, such as flow rate signal 422, crossing a threshold level. Alternatively, the command signal 448 may be generated in response to a clinician selectively stopping the reduced pressure delivery system 402 via a user interface (not shown). Other events, such as a treatment cycle completing, may cause the processing unit to generate the command signal 448 to activate the tissue release valve 446. In another example, a tissue pressure transducer 450 may be used to convert pressure sensed at the tissue site 404 and provide a feedback signal 452 to the processing unit 408 on the PCB 406. In response to the processing unit 408 determining that pressure at the tissue site 404 sensed by the tissue pressure transducer 450 is above a threshold value, the processing unit 408 may communicate command signal 448 to the tissue release valve 446 for release of tissue pressure.

An electronic speaker 454 may be in electrical communication with the PCB 406 to generate an audible sound. In the event that the processing unit 408 determines that a fluid parameter, such as pressure at the tissue site 404 or flow rate of fluid through the reduced pressure conduit 416, crosses a threshold value, a signal 456 may be generated by the PCB 406 and communicated to the electronic speaker 454 to create an audible sound. For example, the processing unit 408 may determine that a fluid leak exists at the tissue site 404 by a fluid rate increasing above a flow rate threshold level. In response to determining that the flow rate level sensed by a flow transducer, such as flow transducer 420, the processing unit 408 may generate the signal 456, such as an alert signal, and communicate the alert signal to the electronic speaker 454 to notify a clinician that a problem exists. In another example, a sensor, such as tissue pressure transducer 450, may sense a fluid parameter at the tissue site 404 and the processing unit 408 may determine that the pressure at the tissue site 404 decreases. Still yet, rather than directly sensing a fluid parameter, an indirect measurement may be performed by measuring duty cycle or power of the pump 410 to determine approximate fluid flow. The processing unit 408 may be selectively programmed or commanded into a fluid leak location mode to enable the clinician to locate the fluid leak at the drape 440 by applying a force on the edges of the drape 440. The processing unit 408 may generate a continuous or discontinuous fluid leak location signal and drive the electronic speaker 454 to enable the clinician to determine a location of the fluid leak at the drape 440.

Although the fluid leak location mode is helpful for locating a fluid leak at the drape, it should be understood that the fluid leak location mode may enable the clinician or technician to locate a fluid leak at the reduced pressure delivery system. For example, should a leak occur at a conduit connection or at a seal, the fluid leak location may help in locating such a fluid leak. In one embodiment, an adapter (not shown) may be provided to cause reduced pressure conduits to simulate operation with a complete drape seal to enable locating a fluid leak at or within the reduced pressure delivery system.

Figure 5:
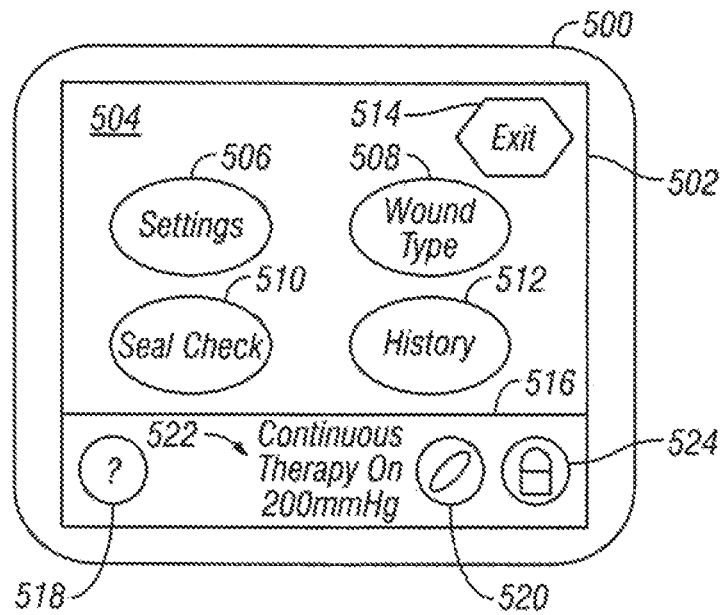
FIG. 5 is a screen shot of an exemplary graphical user interface that enables a clinician to select a "seal check" function to locate fluid leaks that exist at the drape.

With respect to FIG. 5, a reduced pressure delivery system 500 may include an electronic display 502 that is configured to display a graphical user interface (GUI) 504. The GUI 504 may include a number of selectable graphical elements, including a "settings" soft-button 506, "wound type" soft-button 508, "seal check" soft-button 510, and "history" soft-button 512. A user may select any of these functions (i.e., settings, wound type, seal check, or history), to cause the reduced pressure delivery system 500 to present the user with another graphical user interface for performing the selected function. In addition, an "exit" soft-button 514 may be available to the user to exit the current GUI 504. It should be understood that the GUI 504 is exemplary and that other and/or alternative functions and selection elements may be provided to the user.

An information region 516 on the GUI 504 may include selectable graphical elements and display other information in which the user may be interested. For example, a "help" soft-button 518 may be displayed to enable the user to receive help about the reduced pressure delivery system 500 or particular functions currently being displayed on the GUI 504. An "on-off" soft-button 520 may enable a user to selectively turn the reduced pressure delivery system 500 on and off, and information 522 may notify the user of current status of the reduced therapy delivery system 500. For example, the status information 522 may indicate that the reduced therapy delivery system 500 is (i) operating in a continuous therapy mode, (ii) is on, and (iii) is operating to provide a reduced pressure of 200 mmHg. A "lock" soft-button 524 may enable the user to lock the GUI 504 to prevent an inadvertent contact with the GUI 504 to cause the reduced therapy delivery system 500 to respond.

Figure 6A:
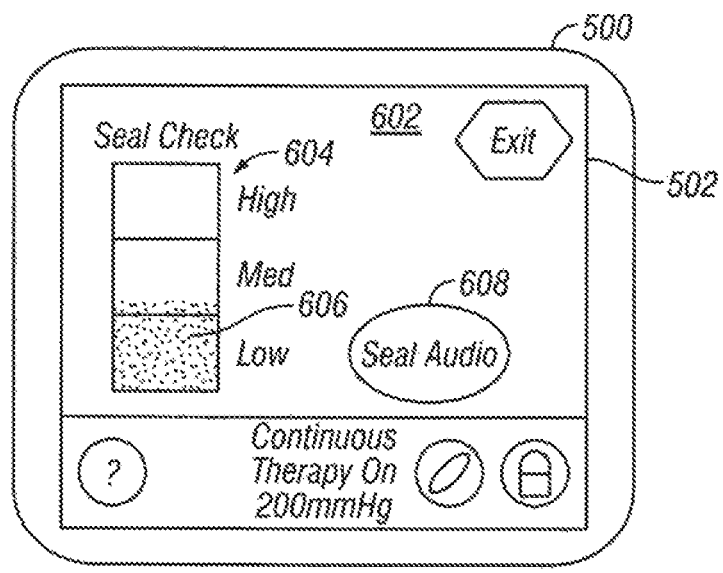
FIG. 6A is a screen shot of another exemplary graphical user interface of a reduced pressure delivery system showing an embodiment for enabling a clinician to select a mode for the reduced pressure delivery system to determine whether any fluid leaks exist at the drape.

With regard to FIG. 6A, the reduced pressure delivery system 500 may display GUI 602 on the electronic display 502 in response to a user selecting the "seal check" soft-button 510 on the GUI 504 of FIG. 5. The GUI 602 may display a graphical indicator 604 indicative of a fluid parameter, such as fluid pressure or fluid flow rate, being sensed by a sensor of the reduced pressure delivery system 500. As shown, the graphical indicator 604 is a bar indicator having three levels, including low, medium, and high. The graphical indicator 604 may show a dynamic portion 606 that increases and decreases based on the fluid parameter being sensed by the sensor (e.g., flow rate sensor or pressure sensor) of the reduced pressure delivery system 500. The height of the dynamic region 606 may indicate the amount of fluid leak currently being sensed at a tissue site. Although the graphical indicator 604 may be helpful to a clinician to determine location of a fluid leak at a drape covering a tissue site, depending upon the arrangement of the reduced pressure delivery system 500 at a patient's bed, a clinician may or may not be able to view the graphical indicator 604 as he or she is attempting to locate a fluid leak at the drape.

So that the clinician may more easily locate the fluid leak at the drape, the reduced pressure delivery system 500 may generate an audible sound indicative of a level of a fluid parameter sensed by a sensor of the reduced pressure delivery system 500. The clinician may select a "seal audio" soft-button 608 to toggle or mute and unmute an audible fluid leak location sound off and on (i.e., mute and unmute). The audible fluid leak location sound may be altered in response to the fluid parameter being sensed changing. For example, if pressure at the tissue site increases in response to the clinician pressing on the drape, the audible fluid leak location sound may be altered to indicate to the clinician that the fluid leak is being or has been sealed and, therefore, located. The audible fluid leak location sound may change in frequency, volume, or pitch. Alternatively, a "Geiger counter" sound may be produced during the seal check, where a tone speed increases or decreases depending upon the change of fluid parameter. For example, if the clinician is "cold" with respect to the location of the fluid leak, the Geiger counter sound may beep slowly. When the clinician presses at or near the fluid leak of the drape, then the Geiger counter sound may increase as the pressure at the tissue site as the fluid leak is sealed until a continuous tone occur when the drape is completely sealed and a maximum pressure or pressure above a seal pressure threshold level is achieved. In another embodiment, the audible fluid leak location sound may be a recorded message, such as "cold," "warmer," and "hot." In another example, a "water dripping" sound may be generated to represent that a fluid leak (e.g., air leak) exists. It should be understood that nearly any sound may be utilized to indicate to the clinician that a fluid leak exists or is being sealed to help the clinician locate the fluid leak. Because a human ear is more sensitive than human eyes, the use of an audible sound to indicate status of a fluid parameter may enable the clinician to more easily determine location of the fluid leak at the drape than a graphical indicator. As understood in the art, gas (e.g., air) is primarily the fluid that is leaked at the drape.

Figure 6B:
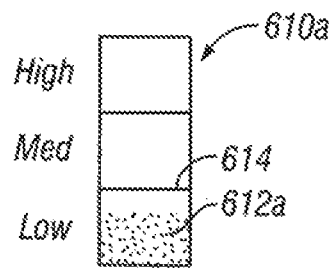
FIGS. 6B-6I are depictions of exemplary indicators for display on the graphical user interface of FIG. 6A to enable a clinician to view while locating a fluid leak at a drape.
Figure 6C:
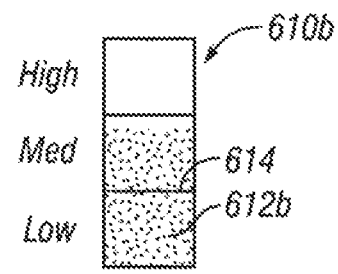

With regard to FIG. 6B, a bar indicator 610a may display a dynamic region 612a indicative of a level of fluid leakage parameter (e.g., pressure). The dynamic region 612a is shown to be within a "low" fluid leakage level and have a corresponding pattern (e.g., lightly shaded) or color (e.g., green). A threshold level indicia 614 may be representative of a threshold level that may be preset by a clinician or manufacturer of the reduced pressure delivery system 500 of FIG. 6A, where an alarm or other response may be generated in response to the fluid leakage parameter crossing the threshold level. As shown on the bar indicator 610a in FIG. 6C, the dynamic region 612b increases above the threshold level indicia 614, thereby, in one embodiment, causing an alarm to be generated and the reduced pressure delivery system 500 to enter into a leak location mode to enable a clinician to locate a leak at the drape or elsewhere. The dynamic region 612b may be changed in pattern (e.g., medium shade) or color (e.g., yellow) to represent that the fluid parameter is currently in the medium range. If, for example, the fluid parameter increases to cause the dynamic region 612 to enter into a high range, then the dynamic region 612 may be changed in pattern (e.g., solid color) or color (e.g., red). Other graphical features may be used, such as flashing or otherwise, to provide the clinician with visual information to make it easier to locate a fluid leak at the drape.

Figure 6D:
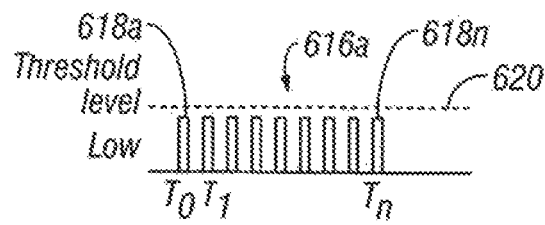
Figure 6E:
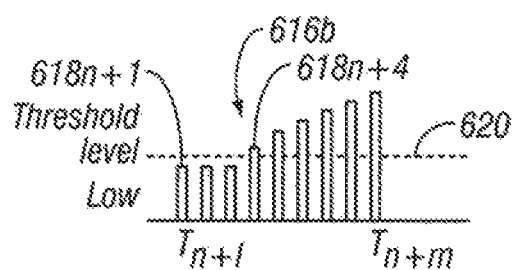

With regard to FIG. 6D, a time sequence 616a is shown to include a number of graphic bars 618a-618n over a time period between time $T_0$ and $T_n$. Graphic bars 618a-618n indicate that the fluid parameter is stable and at a low fluid leakage level. However, as shown in FIG. 6E, graphic bar 618n+4 at time $T_{n+4}$ increases above threshold level 620.

Figure 6F:
Figure 6G:

With regard to FIGS. 6F and 6G, a fluid leakage rate is shown alpha-numerically in display fields 622a and 622b, respectively. As shown, the fluid leakage rate is at "1," which represents a low level leakage, in FIG. 6F and "5," which represents a higher level leakage, in FIG. 6G. In one embodiment, ranges between 0-3 may represent a low level leakage, 4-6 may represent a medium level leakage, and 7-10 may represent a high level leakage. Each level of leakage may represent a corresponding flow rate or pressure level and the digits may change color (e.g., green, orange, and red) depending on the fluid leakage level. In an alternative embodiment, letters, such as "A"-"F," may be displayed.

Figure 6H:
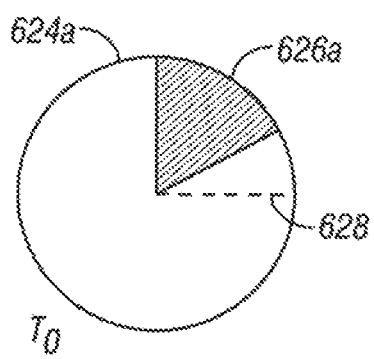
Figure 6I:
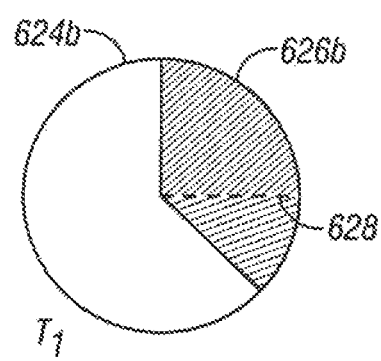

With regard to FIGS. 6H and 6I, pie charts 624a and 624b, respectively, may be displayed that show leakage levels 626a and 626b, respectively, that indicate fluid leakage during operation of a tissue treatment system. One or more threshold levels 628 may be shown and used to identify when a fluid leakage exceeds the threshold, thereby causing a fluid leakage alarm to be initiated. If multiple threshold levels are used, each may represent a different leakage level (e.g., low, medium, or high) and may cause a different alarm, audible and/or visual, to be initiated. Depending on the level of the fluid leakage rate, the color or pattern may change. In addition, an audible sound may be altered in response to the fluid leakage rate increasing or decreasing above or below a threshold level.

With regard to FIG. 7, a process 700 for determining location of a fluid leak is provided. The process 700 starts at step 702, where a reduced pressure may be applied to a tissue site. At step 704, a fluid parameter associated with the reduced pressure may be sensed. The fluid parameter may include a fluid flow rate, fluid pressure, or otherwise. In one embodiment, the fluid parameter is sensed at the tissue site. In another embodiment, the fluid parameter is sensed in a reduced pressure conduit of the reduced pressure delivery system. It should be understood that the fluid parameter may be sensed by any type of sensor that is sensitive enough to sense changes in the fluid parameter that are meaningful to a clinician when attempting to locate and seal a fluid leak. For example, a fluid flow transducer may be configured to sense changes in fluid flow rate between approximately 0.1 liters per minute and 2.0 liters per minute and have a resolution of approximately 0.01 liters per minute.

At step 706, an audible fluid leak location sound may be generated in response to sensing the fluid parameter. The audible fluid leak location sound may be one of a variety of different sounds. Continuous tones with varying frequency, pitch or volume, for example, may be utilized. Alternatively, discrete tones with varying length or frequency may be utilized. Still yet, recorded messages, sounds, or otherwise may be utilized. It should be understood that any sound or combination of sounds may be utilized as an audible fluid leak location sound. At step 708, the audible fluid leak location sound may be altered in response to sensing fluid parameter changes. The altered audible fluid leak location sound may be altered in frequency, pitch, volume, or otherwise. By altering the audible fluid leak location sound, the clinician attempting to locate a fluid leak at the drape may more easily determine the location of the fluid leak, thereby enabling the fluid leak to be sealed.

With regard to FIG. 8, a process 800 for determining a location and reducing a fluid leak at a drape may be performed. The process 800 may start at step 802, where a determination that a fluid leak exists at a drape may be made. A fluid leak alarm may be generated by a reduced pressure delivery system in response to a fluid parameter increasing above or below a threshold level. At step 804, a clinician may listen to an audible sound. The audible sound may be an audible fluid leak location sound that is started in response to the fluid leak being automatically determined or by the clinician selecting to operate a seal check via a graphical user interface. At step 806, the clinician may apply a force to the drape covering the tissue site. The force may be applied by the clinician's finger pressing on a spot at a perimeter location of the drape. The clinician may listen for a change in the audible sound in response to applying the force to the drape at step 808. The clinician may continue to apply force to different locations on the drape and listen for changes in the audible sounds in response to applying the force at different locations of the drape until a determination of a location of the fluid leak at the drape may be made at step 810. The audible sound may indicate that the fluid leak has been sealed at step 812.

Figure 9:
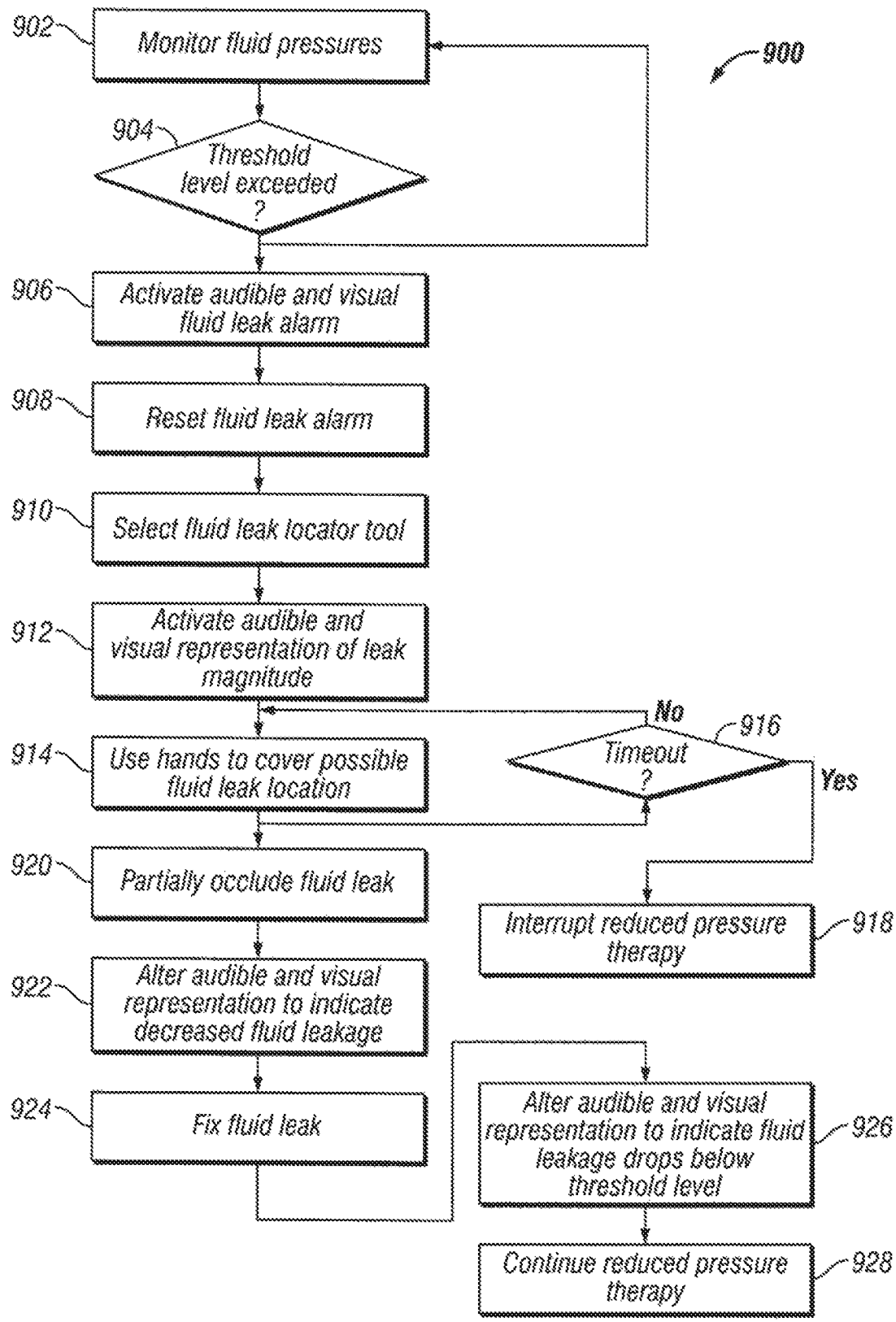
FIG. 9 is a flow chart of an exemplary process for locating and correcting a fluid leak in accordance with the principles of the present invention.

Regarding FIG. 9, an exemplary process for locating and correcting a fluid leak is provided. The process starts at step 902, where fluid pressures are monitored. The fluid pressures may be monitored using a pressure transducer or otherwise. At step 904, a determination as to whether a pressure threshold level is exceeded is made. If the pressure threshold level is not exceeded, then the process returns to step 902. If the pressure threshold level is exceeded, then the process continues at step 906, where an audible and visual fluid leak alarm is activated or otherwise initiated. The process continues at step 908, where the fluid leak alarm is reset by a clinician.

At step 910, the clinician may select a fluid leak located tool or function of the tissue treatment system. An audible and visual representation of leak magnitude may be activated at step 912 to show a fluid leak level, or indication thereof from flow rate or pressure being sensed in the tissue treatment system. At step 914, the clinician may use his or her hands or fingers to cover possible fluid leak locations at a drape covering a tissue site. During this time, a time-out determination may be performed at step 916. If the system is not timed-out, then the process repeats step 914. Alternatively, if the system is determined to time-out, then the process continues at step 918, where reduced pressure therapy is interrupted. The process continues at step 920 after step 914 where the fluid leak is at least partially occluded or otherwise stopped. In response to the fluid leak being partially occluded, the audible and visual representation of the fluid leak is altered to indicate the decreased fluid leak at step 922. At step 924, the fluid leak is fixed by the clinician as he or she has been able to locate the fluid leak at the drape. At step 926, in response to the fluid leak being fixed, the audible and visual representation is altered to indicate fluid leakage dropping below a threshold level. At step 928, the reduced pressure therapy is continued.

The previous description is of preferred embodiments for implementing the invention, and the scope of the invention should not necessarily be limited by this description. The scope of the present invention is instead defined by the following claims.

We claim:

1. An apparatus for detecting leaks at a tissue site, comprising:
    a fluid sensor in fluid communication with a sealed space around the tissue site and configured to sense a fluid parameter within the sealed space and to generate a fluid sensor signal in response to sensing the fluid parameter;
    a processing unit configured to receive the fluid sensor signal and to enter a fluid leak location mode in response to the fluid sensor signal crossing a threshold value; and
    an electronic display in communication with the processing unit and configured to provide a graphical user interface for displaying output related to the fluid leak location mode.

2. The apparatus according to claim 1, wherein the fluid sensor is an airflow sensor.

3. The apparatus according to claim 1, wherein the fluid sensor is a pressure sensor.

4. The apparatus according to claim 1, further comprising a speaker in communication with the processing unit, wherein the processing unit is further configured to communicate a fluid leak location signal to the speaker to generate an audible sensory indicator in a variable manner.

5. The apparatus according to claim 4, wherein the processing unit is further configured to, in response to the fluid sensor signal being altered, change the fluid leak location signal in the variable manner.

6. The apparatus according to claim 5, wherein the processing unit is configured to alter an audible frequency of the fluid leak location signal.

7. The apparatus according to claim 5, wherein the processing unit is configured to alter a duration of the fluid leak location signal.

8. The apparatus according to claim 5, wherein the processing unit is configured to alter an amplitude of the fluid leak location signal.

9. The apparatus according to claim 4, wherein the processing unit is further configured to:
    generate an alarm signal in response to determining that the fluid sensor signal crossed the threshold value; and
    communicate the alarm signal to the speaker to cause an alarm to be generated.

10. The apparatus according to claim 4, wherein the processing unit is configured to selectively toggle the audible sensory indicator on and off.

11. The apparatus according to claim 1, wherein the processing unit is further configured to display a selectable graphical element on the graphical user interface that enables a user to cause the processing unit to enter the fluid leak location mode.

12. The apparatus according to claim 1, wherein the processing unit is further configured to generate a graphical indicator indicative of the fluid parameter and to change the graphical indicator in response to a change of the fluid parameter while in the fluid leak location mode.

13. The apparatus according to claim 12, wherein the graphical indicator is a numerical value.

14. An apparatus for treating a tissue site on a patient, comprising:
    sensor means in fluid communication with a sealed space around the tissue site for providing a plurality of data outputs based on measurements of a fluid parameter applied to the tissue site;
    processing means for comparing each of the plurality of data outputs to a predetermined value and for enabling a fluid leak location mode to be entered when one of the data outputs equals the predetermined value; and
    communication means for providing a user with an output related to the fluid leak location mode being entered.

15. The apparatus according to claim 14, wherein the communication means is a graphical user interface.

16. The apparatus according to claim 14, wherein the communication means is a speaker.

17. The apparatus according to claim 14, wherein the fluid parameter corresponds to a fluid pressure.

18. The apparatus according to claim 14, wherein the fluid parameter corresponds to a fluid flow rate.

19. A method for detecting leaks at an interface between a tissue site and a tissue dressing, comprising:
    sensing a fluid parameter being applied to the tissue site;
    generating a fluid sensor signal in response to sensing the fluid parameter;
    entering a fluid leak location mode in response to the fluid sensor signal crossing a threshold value;
    providing an output related to the fluid leak location mode for communicating to a user.

20. The method according to claim 19, wherein sensing the fluid parameter includes sensing airflow.

21. The method according to claim 19, wherein sensing the fluid parameter includes sensing pressure.

22. The method according to claim 19, wherein providing the output related to the fluid leak location mode comprises generating an audible fluid leak location sound in a variable manner.

23. The method according to claim 22, further comprising altering the audible fluid leak location sound in the variable manner in response to receiving an altered fluid sensor signal.

24. The method according to claim 23, wherein altering the audible fluid leak location sound comprises altering an audible frequency of the audible fluid leak location sound.

25. The method according to claim 23, wherein altering the audible fluid leak location sound comprises altering a duration of the audible fluid leak location sound.

26. The method according to claim 19, wherein providing the output related to the fluid leak location mode comprises displaying a graphical indicator on a graphical user interface, wherein the graphical indicator is indicative of the fluid parameter.

27. The method according to claim 26, further comprising changing the graphical indicator in response to a change of the fluid parameter while in the fluid leak location mode.

28. The method according to claim 26, wherein the graphical indicator is a numerical value.

29. The method according to claim 28, wherein the numerical value is dynamically altered in response to the fluid sensor signal changing.

\* \* \* \* \*